US005639632A

United States Patent [19]
Ericsson et al.

[11] Patent Number: 5,639,632
[45] Date of Patent: Jun. 17, 1997

[54] METHOD AND DEVICE FOR STUDYING AND QUANTIFYING INTERACTING EFFECTS OF SUBSTANCES ON BIOLOGICAL CELLS

[75] Inventors: Magnus Ericsson, Stockholm; Anne Bolmström, Åkersberga, both of Sweden

[73] Assignee: AB Biodisk, Solna, Sweden

[21] Appl. No.: 389,749

[22] Filed: Feb. 14, 1995

Related U.S. Application Data

[63] Continuation of Ser. No. 17,991, Jul. 16, 1993, abandoned, which is a continuation of Ser. No. 487,448, Mar. 2, 1990, abandoned.

[51] Int. Cl.[6] .................................................. C12Q 1/18
[52] U.S. Cl. ........................ 435/32; 435/29; 435/34; 435/287.1; 435/288.3; 436/63
[58] Field of Search .......................... 435/29, 30, 32, 435/33, 34, 297, 299, 287.1, 287.3, 287.9, 288.3, 288.7; 436/63; 422/55, 57

[56] References Cited

U.S. PATENT DOCUMENTS 4,054,490 10/1977 Vesterberg .
4,778,758 10/1988 Ericsson et al. .
4,820,292 4/1989 Korol ............................................ 435/32
5,028,529 7/1991 Ericsson et al. .

FOREIGN PATENT DOCUMENTS 157071 10/1985 European Pat. Off. .
389164 6/1965 Switzerland .

OTHER PUBLICATIONS

Linnette et al Manual of Clinical Microbiology 1980 pp. 478–484.
Bird Infection and Immunity v55 N3 pp. 771–777.
E.J. Stokes et al., *Clinical Microbiology*, 1987, pp. 225–233.
Krogstad et al., "Combinations of Antibiotics, Mechanisms of Interaction Against Bacteria", *Antibiotics in Laboratory Medicine*, Lorain, 1986, Chapter 11, pp. 298–341.

Primary Examiner—Milton Cano
Attorney, Agent, or Firm—Burns, Doane, Swecker & Mathis

[57] ABSTRACT

Device and method for quantitative determination of the interacting effects of two or more substances on the promotion or inhibition of growth of microorganisms or other biological cells grown on a solid medium, wherein the substances are applied within a quadrate test area in the solid medium in predefined concentration patterns having concentration perimeters exhibiting maxima and minima at opposite edges of the test area and with the concentration gradient directions of the substances perpendicular to each other.

12 Claims, 11 Drawing Sheets

METHOD AND DEVICE FOR STUDYING AND QUANTIFYING INTERACTING EFFECTS OF SUBSTANCES ON BIOLOGICAL CELLS

This application is a continuation of application Ser. No. 08/017,991, filed Feb. 16, 1993, which is a continuation of application Ser. No. 07/487,448, filed Mar. 2, 1990, both now abandoned.

FIELD OF THE INVENTION

The present invention concerns a method and a device for studying and quantifying the interacting effects of two or more substances on the inhibition or promotion of growth of microorganisms or other biological cells.

Combinations of antimicrobial agents are used for the treatment of infectious diseases in many situations. Most frequently, combinations of antimicrobial agents, e.g. two antibiotics, a combination of an antibiotic and a chemotherapeutcal agent or antibiotic combinations are used to provide broad spectrum coverage in seriously ill patients before the infecting pathogen(s) have been identified. In polymicrobial infections no one drug may be active against the different organisms present and antibiotic combinations will be required to eradicate the mixture of pathogens. Two antibiotics may also be given to prevent or at least delay the development of resistance to either compound for example in the treatment of tuberculosis. Treatment of urinary tract infections are often carried out with a combination of chemotherapeutical agents, e.g. trimethoprim/sulphamethoxazol or trimethroprim/sulphadiazine. Antibiotic combinations may also be required to achieve a synergistic effect in the treatment of serious infections such as endocarditis and septicaemia. A particular situation where combined therapy is preferred to monotherapy even when the causal organism is known, is that of febrile patients being treated with immunosuppressants.

When two or more drugs are given together, many different interactive effects may be seen. The substances may affect each other per se, such as an inactivation of one antibiotic by another e.g. the inactivation of gentamicin by carbenicillin when stored in the same infusion bottle before administration. Another is the interaction between antineoplastic agents with known antimicrobials where adverse effects may be devastating in the treatment of cancer patients.

The effects of antibiotic combinations on bacteria fit three major descriptions. Firstly, interactions may be indifferent when the activity of both drugs are unaffected by the presence of the other. Secondly, interactions may be synergistic i.e., the combined effects of both drugs is significantly greater than that of either acting alone in the same concentration. Thirdly, combinations may be antagonistic when the activity of one drug is reduced by the presence of the other.

Although much emphasis is placed on the demonstration of synergistic effects, it is just as important to ensure that antagonism does not occur. Synergistic and antagonistic effects of antibiotic combinations may occur in varying ratios of the two compounds. Combination therapy with potentially toxic antibiotics such as aminoglycosides e.g. gentamicin have to be administered in correct dosages to avoid dose-related drug toxicity. Thus laboratory tests to study the effects of antibiotic combinations should provide both qualitative and quantitative information about which combinations to prescribe and which optimal dosages and dose-ratios to use.

Similar to the concept of antibiotic combinations is the interactive effects of other substances which may promote or retard the metabolism and growth of microorganisms and other biological cells. Studies involving growth promoters and other biological nutrients are useful for the design of media formulations. The carcinogenic, mutagenic and teratogenic effects of drug-drug combinations are also studied in the development of new drugs for clinical use.

DESCRIPTION OF RELATED ART

In U.S. Pat. No. 5,028,529 is described a device and a method for determination of i.a. synergistic and antagonistic effects of active substances. However, the device and method disclosed therein do not lead to a quantitative determination in respect of the determination of the interacting effects and can thus not be used for determination of therapeutic dosage levels for the active substances.

Quantitative determinations of the combined effects of antibiotics are mainly carried out with the checkerboard or chessboard method as described by Krogstad et al in Antibiotics in Laboratory Medicine, Lorian, 1986. These methods are technically cumbersome, time-consuming and very expensive to carry out.

Checkerboard titrations involve exposing the test organism to serial two-fold dilutions of two antibiotics so that all possible combinations of drug concentrations (within the range of dilutions used) are tested. The test consist of preparing a range of 10 or more dilutions of each drug starting from just above the expected Minimum Inhibitory Concentration (MIC). The checkerboard consist of columns of test tubes or agar plates which contain the same amount of one drug which is diluted along the X-axis and rows which each contain the same amount of the other drug, diluted along the Y-axis. This is illustrated in FIG. 1, which shows rows of test tubes seen from above. In the tubes the concentrations of the two antibiotics to be tested increase as indicated with the arrows and in the tube to the left at the bottom there is a minimum concentration of both of the substances, whereas the tube to the right in the upper row exhibits a maximum concentration of both substances. Thus each square (tube) in the checkerboard is a unique combination of the two drugs. Dilutions of the antimicrobial agents to be used are usually made in broth or agar. In the example illustrated by this figure there is inhibition in the blank tubes (no growth), whereas there is growth in the turbid tubes.

Checkerboard titrations are extremely laborious and timely to perform. Firstly, the MICs of the two antibiotics to be combined have to be determined in order to select the relevant dilution ranges.

When setting up the checkerboard with for example 15 dilutions of each substance, 225 tubes or agar plates will be required for each determination. The working procedure involves many manual steps where laboratory errors may be introduced such as incorrect dilutions and contamination of working solutions giving inaccurate or even incorrect results. It may take at least 1–2 weeks to obtain results of checkerboard studies and this is a major drawback in the case of seriously ill patients, where delayed selective therapy or incorrect therapy due to empirical choices of potentially antagonistic antibiotic combinations may have a fatal outcome.

SUMMARY OF THE INVENTION

With the present invention, the interactions of two or more antimicrobial agents can be accurately quantified within 1–2 days allowing the physician to select the appropriate antibiotic combinations and in the optimal dose-ratios. The disadvantages of the aforementioned checkerboard methods can be eliminated by this invention which comprises premade, ready to use test systems requiring minimal auxilliary laboratory materials, a few quick steps to set up and giving results which can be directly read and interpreted. The technique of the present invention can thus be routinely used even by non-specialized laboratories making important clinical information on the effects of combinations of antimicrobial agents readily and rapidly available for a safe and effective treatment of serious infections.

In one embodiment of the method of the present invention, the interacting effect of two or more substances on the promotion or inhibition of growth of microorganisms or other biological cells grown on a solid medium are determined by applying the substances within a quadrate test area on the surface of the growth medium and in predefined concentration patterns in such a way that the first substance exhibits a concentration minimum perimeter on one edge and a concentration maximum perimeter on the opposite edge of the quadrate and a second substance exhibits a concentration minimum perimeter on a third edge and a concentration maximum perimeter on the opposite edge of the quadrate, incubating the thus treated plate, reading the inhibition pattern and determining the required concentrations of the two substances at the relevant end points using reading scales that are adapted to the predefined concentration patterns of the substances. Thus, the first substance may have its concentration gradient extending along the Y-axis (i.e. vertical direction) with its maximum value above the minimum value, and the second substance may have its concentration gradient extending along the X-axis (i.e. horizontal direction) with the concentration minimum on the left and maximum on the right hand sides of the X-axis. The direction of concentration gradients of the two substances will thus be perpendicular to each other.

In another embodiment of the method of the present invention one substance is applied in a uniform concentration within a quadrate test area on the surface of the growth medium, whereas the second and further substances are applied as concentration gradients in the way mentioned above.

The two substances are applied on a quadrate test area of the surface of the growth medium by bringing into contact an inert carrier with the medium. The carrier is of a non-porous material and thereon both substances prevail in the desired concentration pattern, thus yielding the predetermined concentration gradients of both substances in the agar medium when the carrier is brought into contact with the agar surface. It is also possible to have separate carriers on which the different substances are immobilized. In such a case, the desired predetermined concentration patterns of the two substances on the agar surface, is achieved when the carrier with the first substance has been applied onto a quadrate test area of the surface of the medium and removed after sufficient time has passed for a complete release of the substance into the medium, whereafter the second substance can be applied by placing a second carrier onto the imprint of the first substance of the agar surface in such a way that the gradient directions of the two substances are perpendicular to each other.

If three or more substances are to be tested together, they may be applied onto the agar, using a the carrier on which all substances prevail in the desired concentration pattern. Equally one or more substances may prevail in the desired concentration pattern on the same carrier, and be successively applied onto the gradient imprints of other substances in the agar.

Examples of carriers suitable for use in the present invention are thin sheets of inert, non-porous material, for example polyacrylic amide, polyester, polyethylene, polyamide, polycarbonate or similar materials. The materials can be opaque or transparent.

In one embodiment of a device according to the present invention a quadrate test area on a carrier is applied with one substance having a concentration gradient extending continuously from a concentration minimum perimeter on one edge to a concentration maxima perimeter on the opposite edge of the quadrate test area on the carrier.

In another embodiment of a device according to the present invention, two substances are applied on a quadrate area on the carrier, and in such a way that the first substance exhibits a concentration minimum perimeter on one edge and a concentration maximum perimeter on the opposite edge and the second substance having a concentration gradient extending in a direction perpendicular to that of the first substance and exhibiting a concentration minimum perimeter on a third edge and a concentration maximum perimeter on the opposite edge of the quadrate test area on the carrier.

In a further embodiment of a device according to the present invention, three or more substances are applied on a quadrate area on the carrier. The first two substances are applied as described above while further substances are successively applied on top of the other two substances. These further substances also exhibit concentration minimum and maximum perimeters on opposite edges of the quadrate test area on the carrier.

In still another embodiment of a device according to the invention one of the substances is applied in a constant concentration on a quadrate area of the carrier, whereas the second and further substances are applied in concentration gradients as mentioned above.

The substances can be applied on the surface of the carrier in a manner known per se, for example by precision micropipetting specific volumes of antibiotic solutions having defined concentrations increasing at successive intervals along the predetermined concentration gradient. Other methods of applying the substances may include ink-jet printing, computer controlled precision spraying or other elaborated coating techniques.

The carrier can be of various shapes and sizes, e.g. square, rectangular or round. The substance can be applied on a quadrate test area of the carrier. Said quadrate test area may comprise the entire carrier or part of the carrier.

Reading scales adapted to the concentration gradients of the substances can be either separate from the carrier or integrated with the carrier. The reading scales are applied on the upper side of the carrier, i.e. the side opposite the surface on which the substances are applied. Further the upper side of the carrier can also be labelled with the name of the substances and other relevant information.

BRIEF DESCRIPTION OF THE DRAWINGS

The present invention is further illustrated by the accompanying figures, where.

DESCRIPTION OF THE PREFERRED EMBODIMENTS

Figure 1:
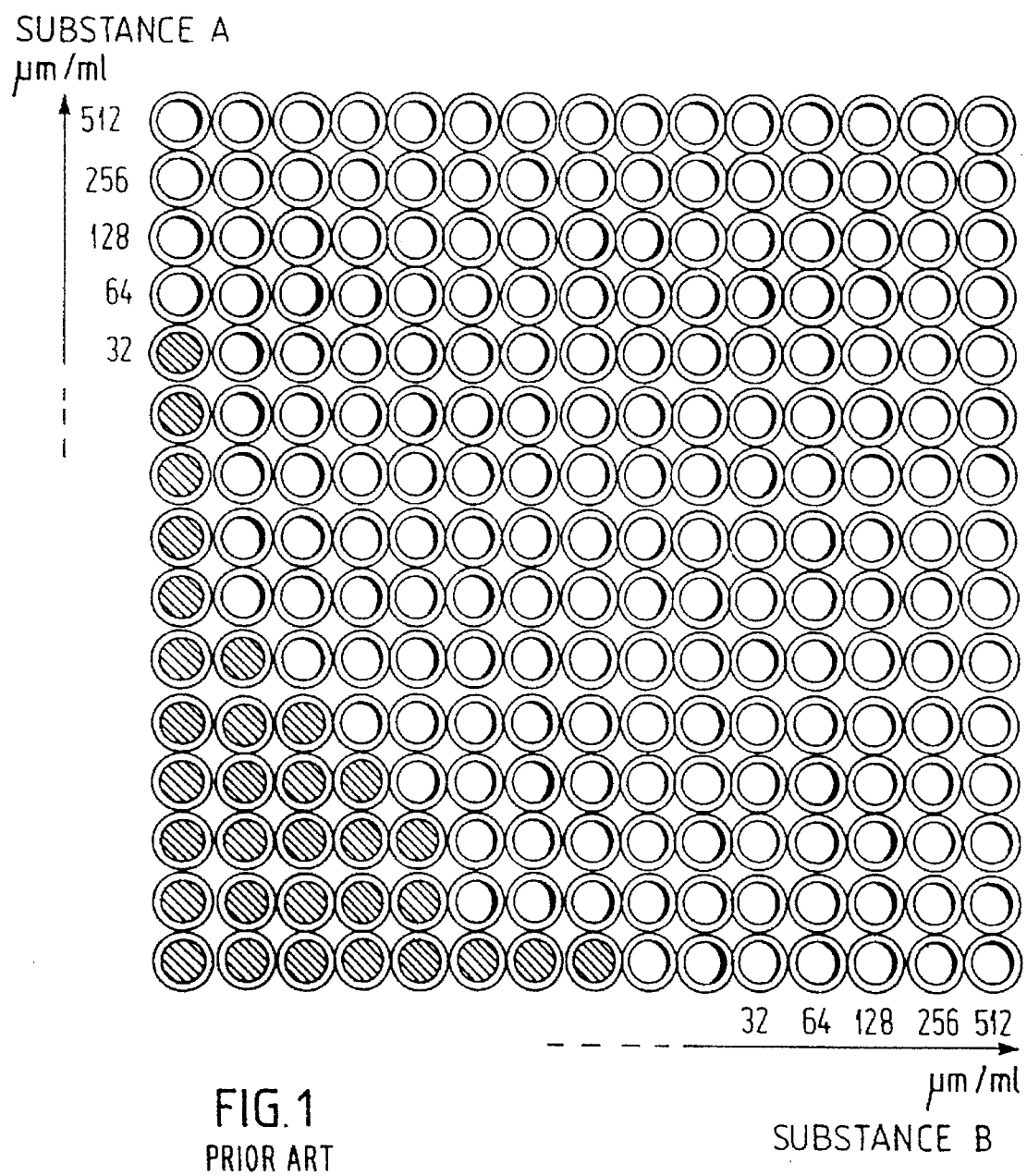
FIG. 1 shows prior art checkerboard titration in test tubes, FIGS. 2 A and B show a device, on which one substance is present, whereas FIGS. 2 C and D show a continuous checkerboard configuration, FIGS. 3 A and B the same checkerboard configuration as in FIG. 2 C, but showing the maximum and minimum concentration perimeters of the substances as well as the isobols of their concentration ratios.
Figure 2A:
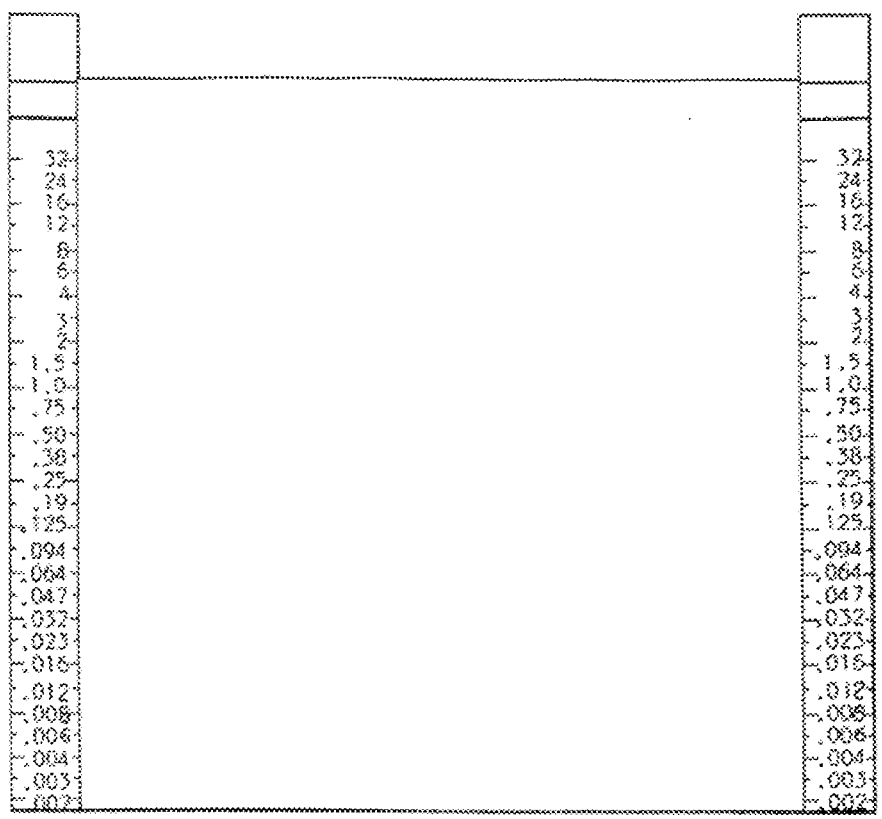
Figure 2B:
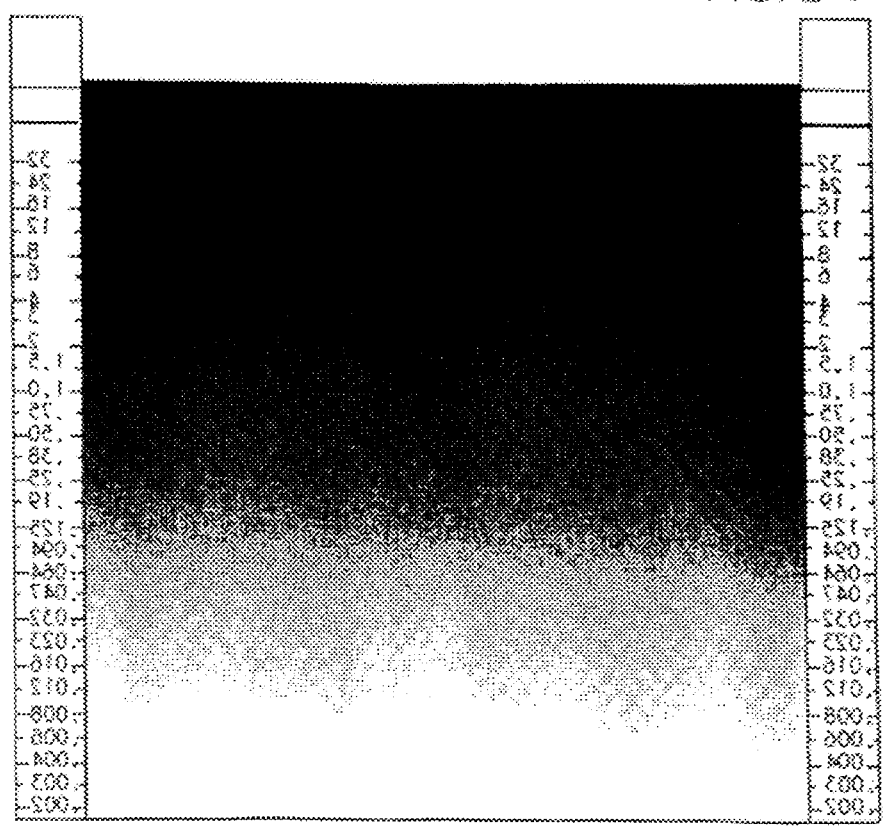
Figure 2C:
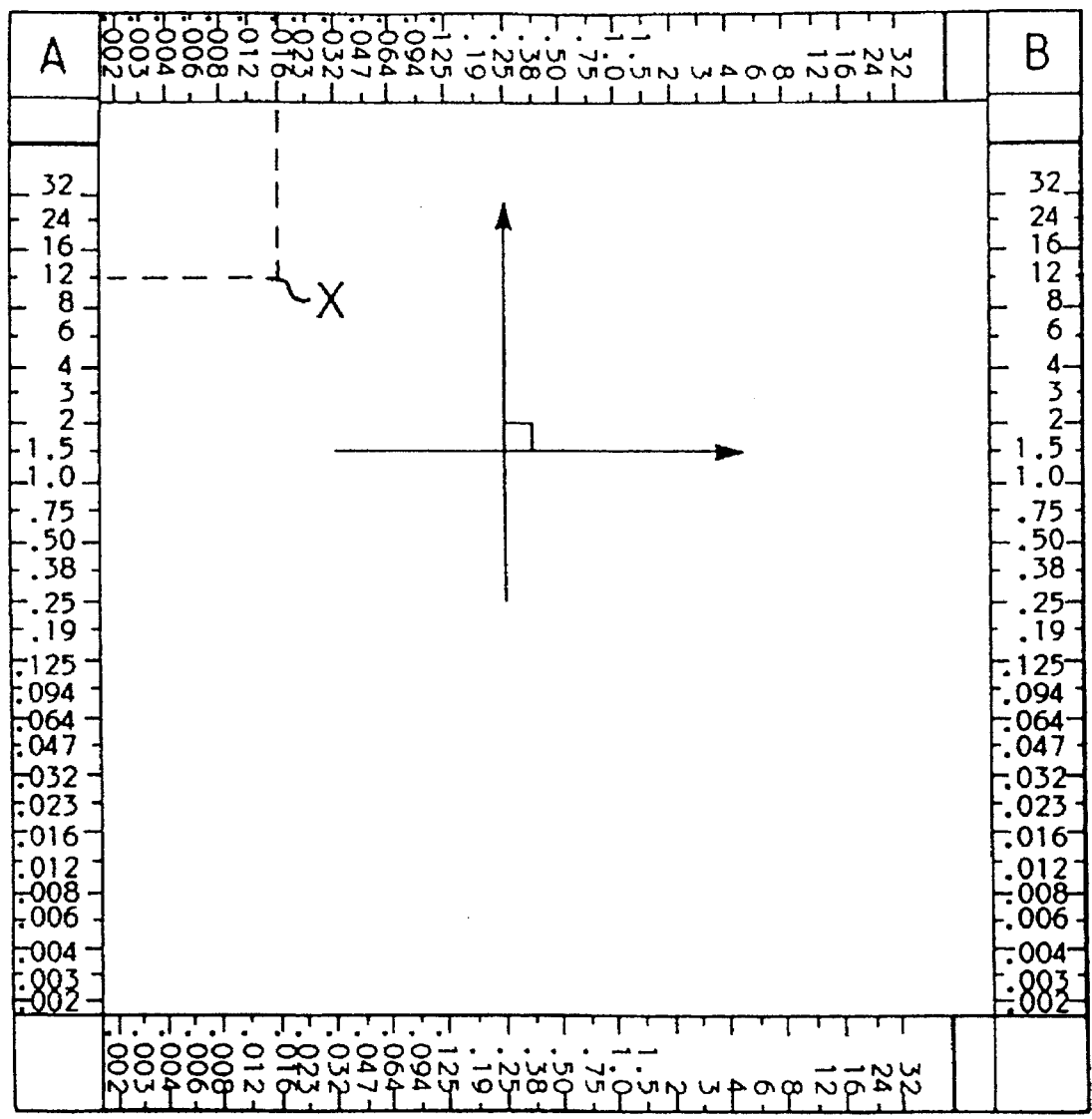
Figure 2D:
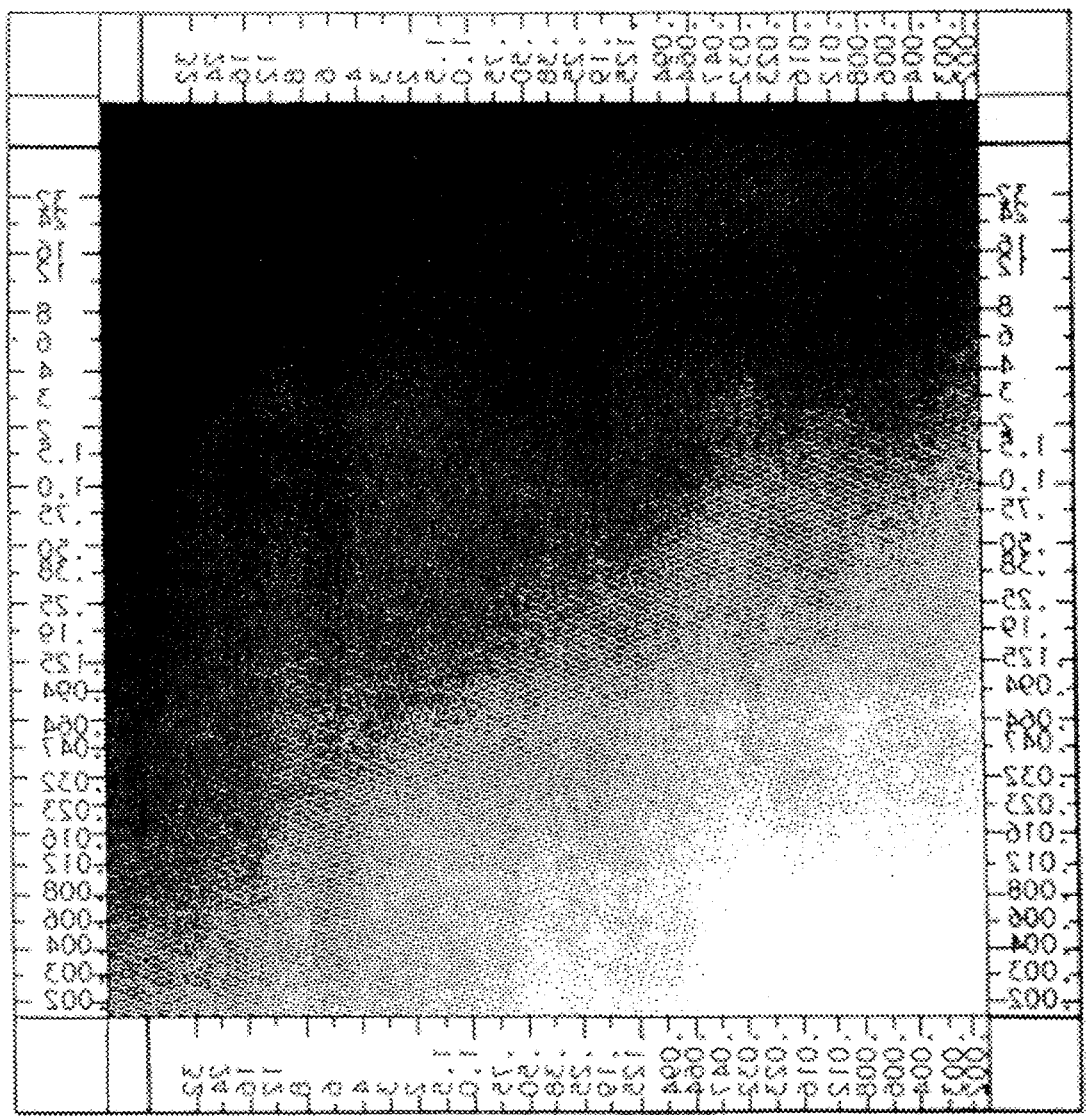

The checkboard configuration show in FIG. 1 is surrounded by reading scales that are adapted to the predefined concentration patterns of the two substances. FIGS. 2 A and B show an embodiment of a device according to the invention on which one substance is applied. FIG. 2 A shows the one side of the device with the reading scale and 2 B shows the other side of the same device where the density of the dots symbolizes the concentration gradient of the substance extending from a maximum perimeter at the top to a minimum perimeter at the bottom of the device. FIGS. 2 C and D show an embodiment in which two substances are present on the device to achieve the checkerboard configuration. FIG. 2c shows one side of the device with the reading scale and 2 D the other side of the device where the density of the dots symbolizes the concentration patterns of the two substances in the checkerboard configuration. In FIG. 2 C the arrows indicate the perpendicular directions of the concentration gradients of the substances. Por illustrative purposes X indicates the point where the concentration of substance A is equal to 12 µg/ml and substance B to 0.016 µg/ml.

Figure 3A:
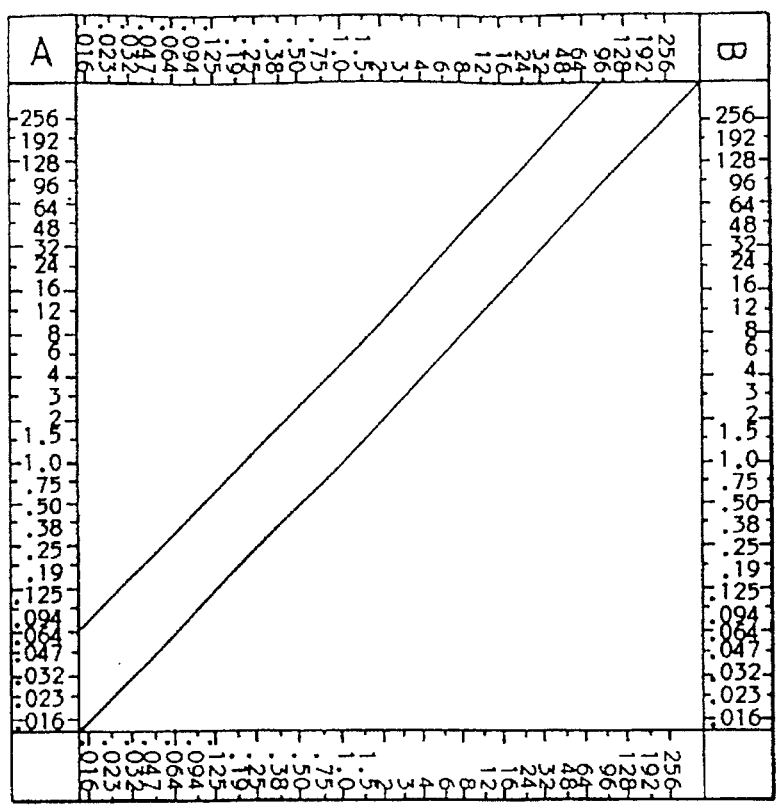
Figure 3B:
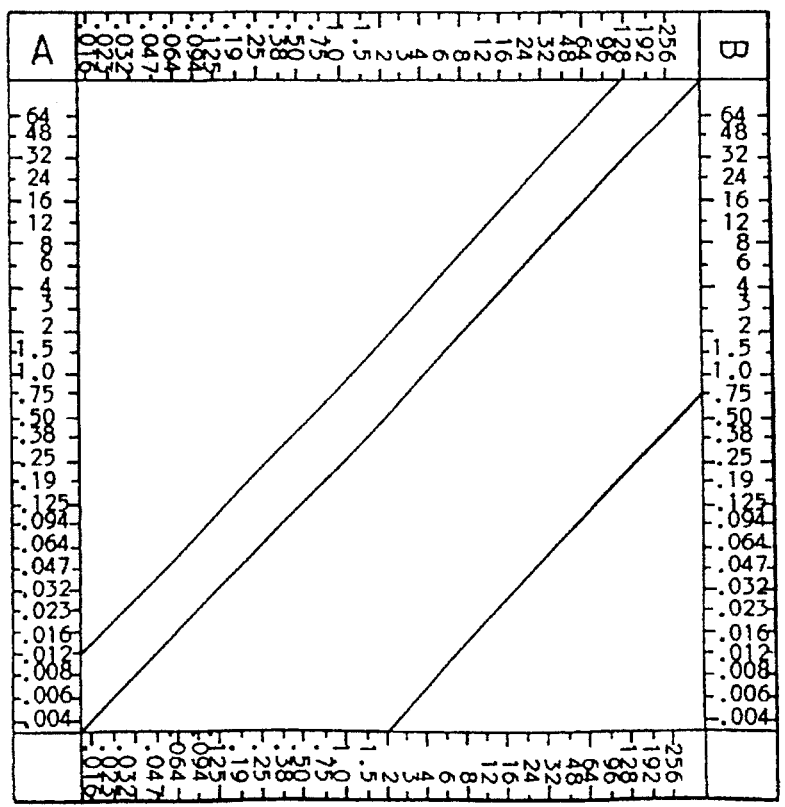

FIGS. 3 A and B show other embodiments of the checkerboard configuration according to the present invention. The checkerboard square is surrounded by reading scales whereby the exact concentrations of the two substances anywhere within the square can be easily interpolated. FIG. 3A shows an embodiment in which the ranges of the concentration gradients of the two substances are equal, (i.e. A and B are present in the range of 0.016 and 256 µg/ml), whereas in FIG. 3B the ranges of the concentration gradients of the substances differ from each other (i.e. A is present from 0.004 to 64 µg/ml and B from 0.16 to 256 µg/ml). The perpendicular directions of the concentration gradients of the two substances A and B results in four corners of the square having superimposed concentration minima of A/B, in the lower left hand corner, and in a clock-wise direction maximum A/minimum B, maxima A/B and maximum B/minimum A. FIGS. 3 A and B show isobols, i.e. the lines connecting the points exhibiting a constant ratio of the substances A and B. An example of an isobol is the diagonal between the concentration minima and maxima which comprises a constant ratio of A and B. Lines parallel to the diagonal constitutes other isobols.

Figure 4A:
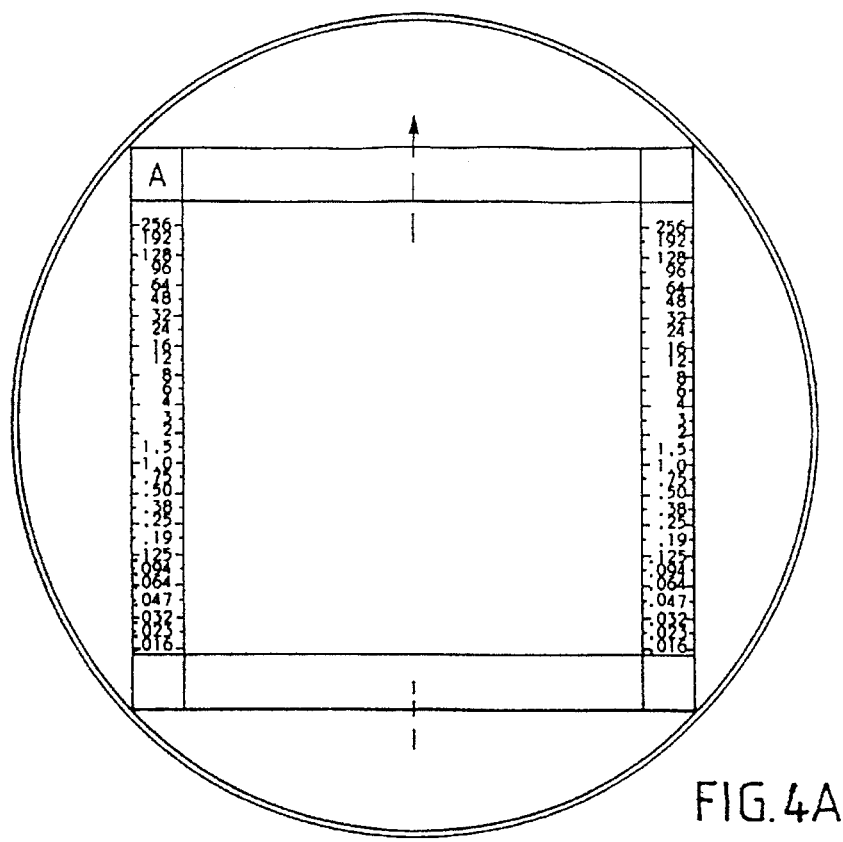
FIGS. 4 A and B show how the substances are succesively applied onto the surface of the medium, using the device of FIGS. 2 A and B.
Figure 4B:
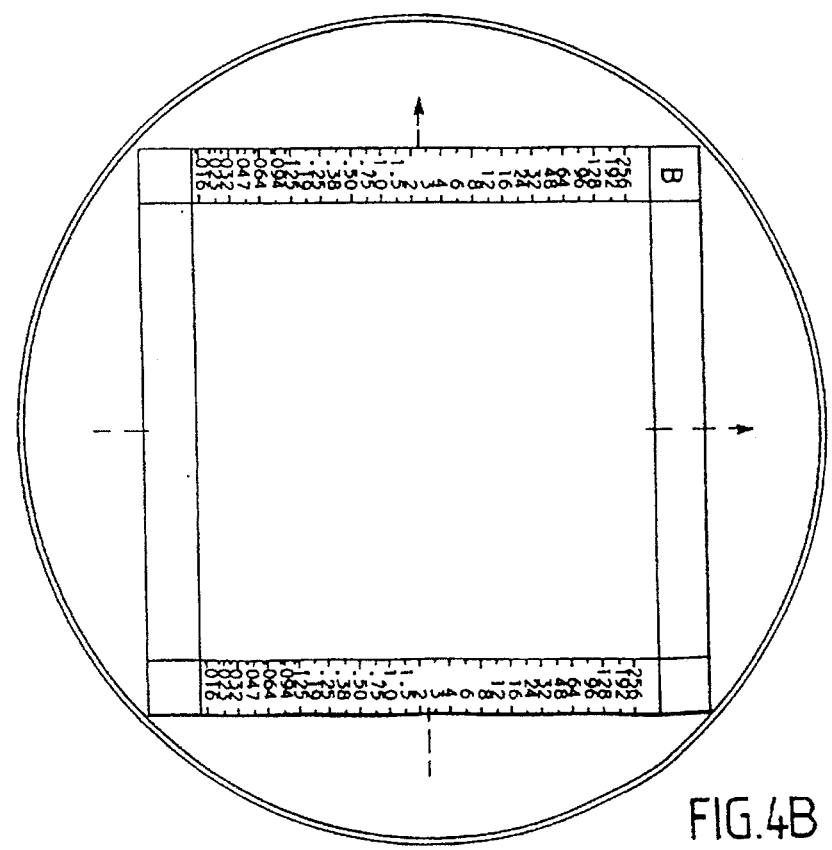
Figure 5A:
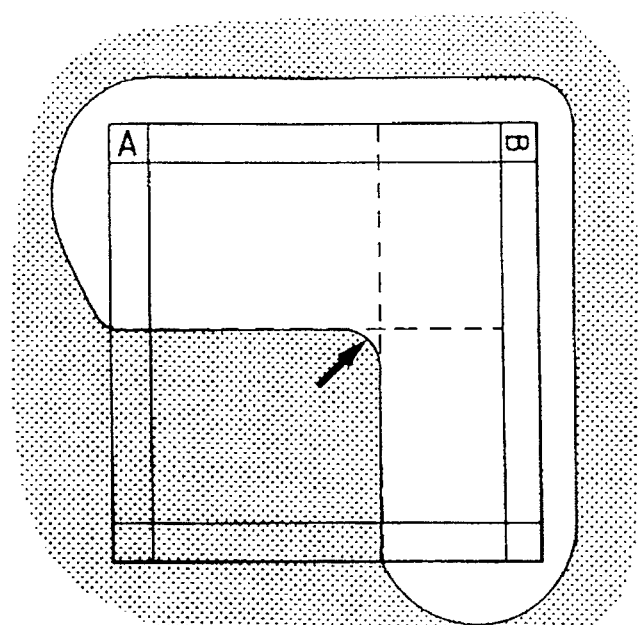
FIGS. 5 A, B, C, D and E show the interpretation of interactions between the substances and FIGS. 6 A and B show how bactericidal interactions can be studied.
Figure 5B:
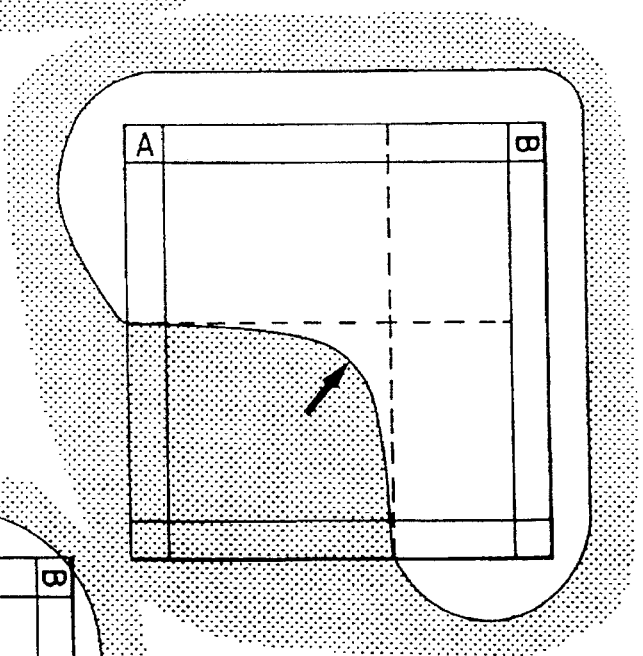
Figure 5C:
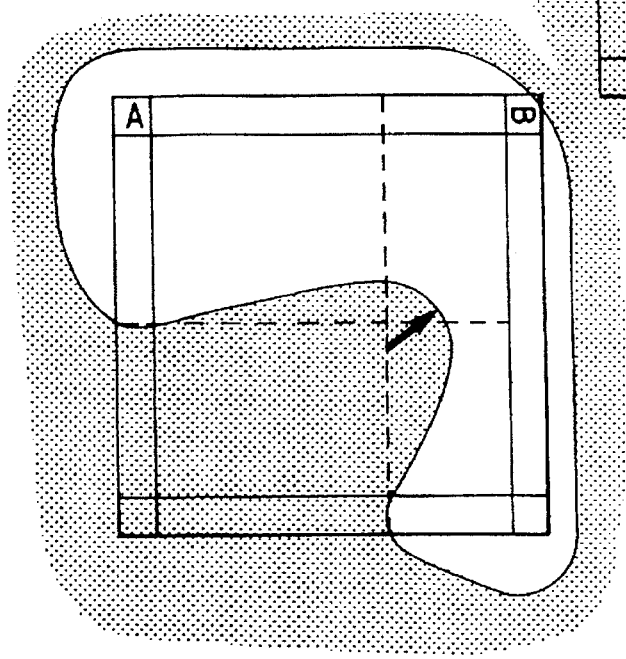
Figure 5D:
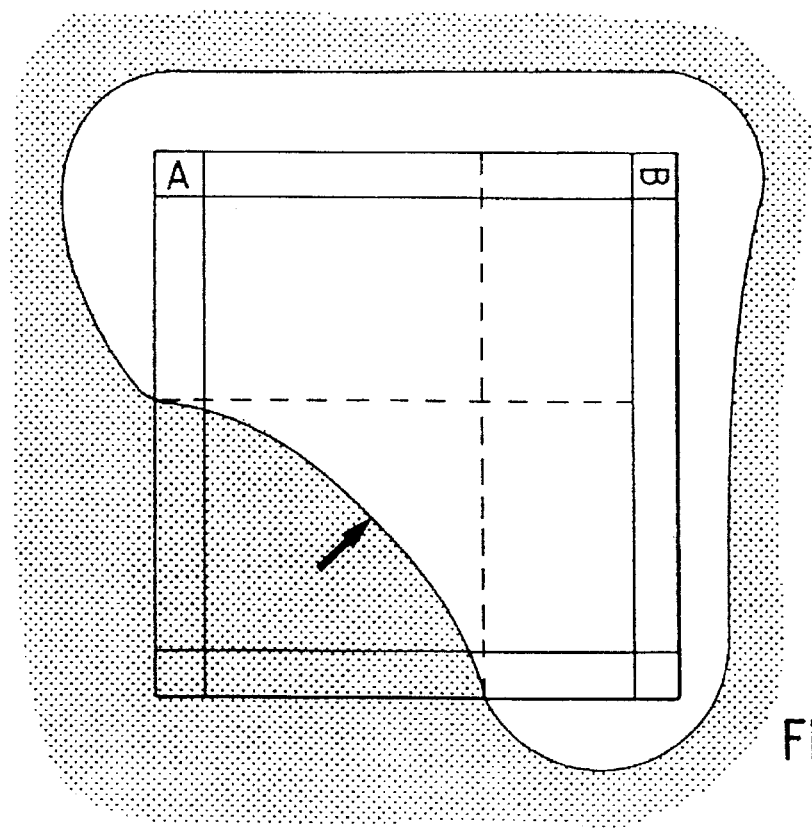
Figure 5E:
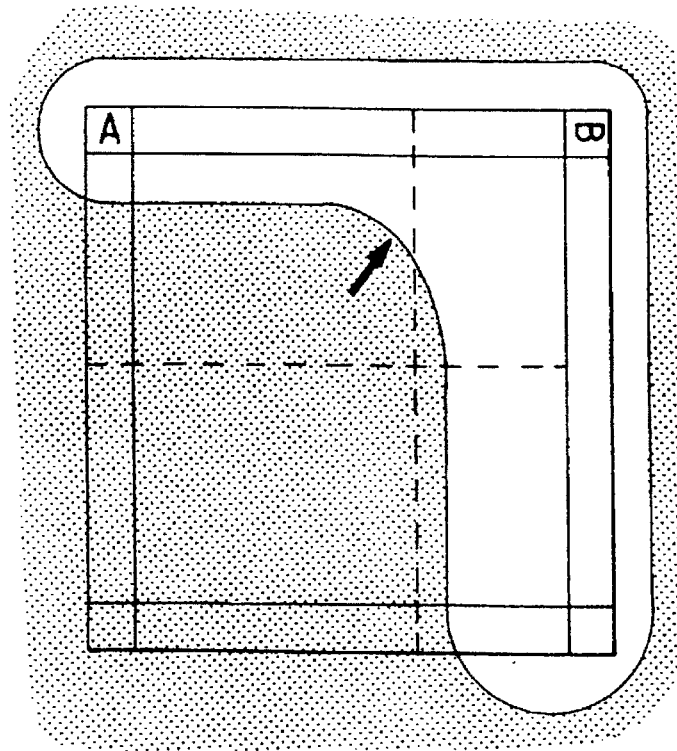

FIGS. 4 A and B show how two substances are applied onto the surface of an agar plate inoculated with bacteria by different methods known per se. These methods may include flooding or swabbing the surface of the agar with the bacterial suspension or seeding the agar with the bacteria, i.e. suspending bacteria in molten agar, pouring it onto the agar surface and allowing the layer to set. The circle representing the Petri-dish and in 4 A a first substance, e.g. an antibiotic, is applied onto the agar surface using a carrier, on which the first substance prevails in a pre-defined concentration pattern, confined to a quadrate area and exhibiting a minimum perimeter on the bottom edge of the test quadrate and a maximum perimeter on the top edge thereof. After the required period for complete release of antibiotic from the carrier surface into the agar matrix, viz. about 1 hour for most antibiotics, the carrier is removed and a second carrier with the second substance is brought into contact with the agar surface exactly on top of the imprint of the first substance (FIG. 4 B). This is done in such a way that the direction of the concentration gradient of the second substance, e.g. another antibiotic, is perpendicular to that of the first substance and that the substance exhibits a concentration minimum along the left edge of the quadrate and a maximum along the opposite edge, i.e. the right edge of the square. In order to facilitate the application of the substances in gradients perpendicular to each other it can be of convenience to have the direction of the gradient marked on the carriers and to mark the direction of the first gradient on the Petri-dish upon the application thereof. Further substances can be applied by a successive removal of carriers after a release of each substance and replacing a new carrier with substance onto the agar imprint of the prior substance. When testing strictly aerobic bacteria, the last carrier is removed after 1 hour and a reading scale in the form of a frame is placed around the quadrate gradient imprint in the agar and the plate thereafter incubated. For anaerobic and facultative anaerobic bacteria, the last carrier may be left in place during incubation and serve as a reading scale. In general the reading scales that are adapted to the predefined concentration patterns of the checkerboard configuration can be applied onto the agar plate either before or after the application of the substances. After overnight incubation, the inhibition patterns are read.

Figure 6A:
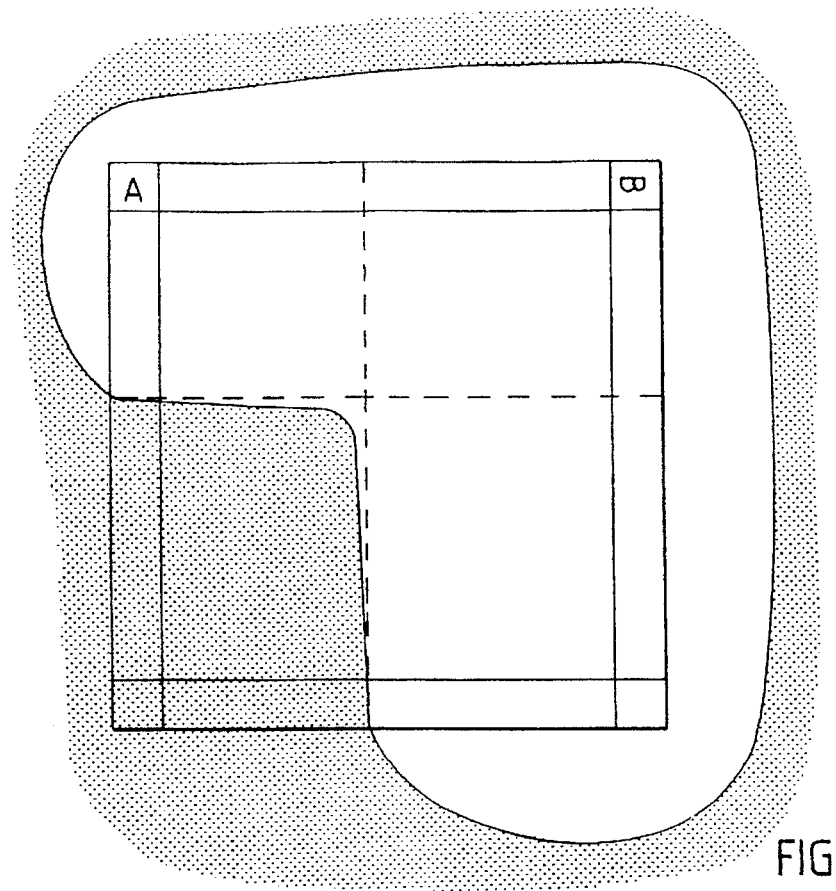
Figure 6B:
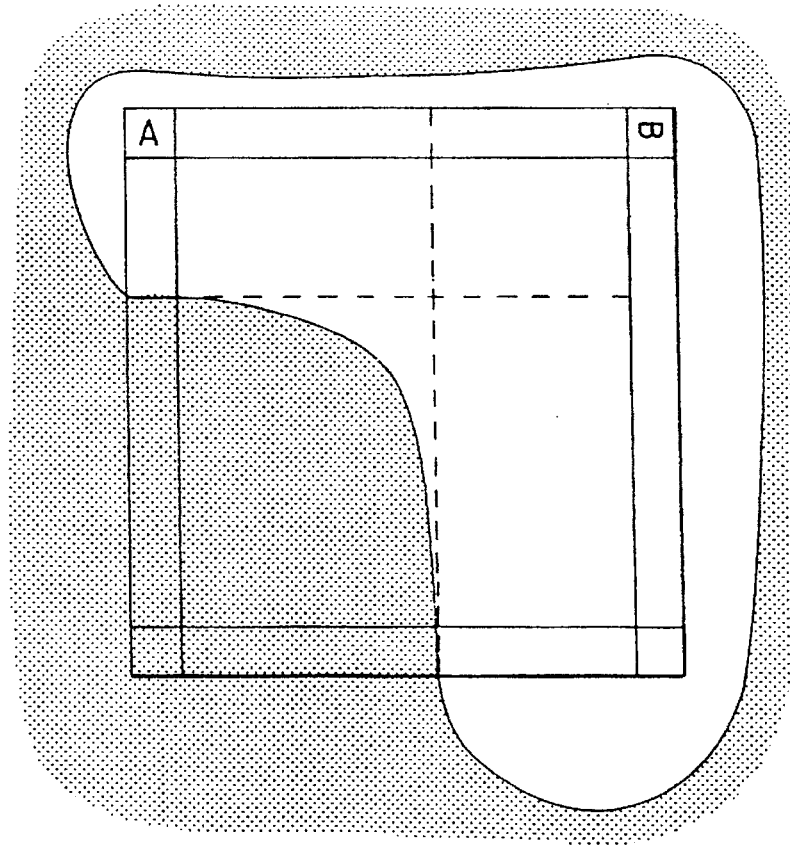
Figure 7:
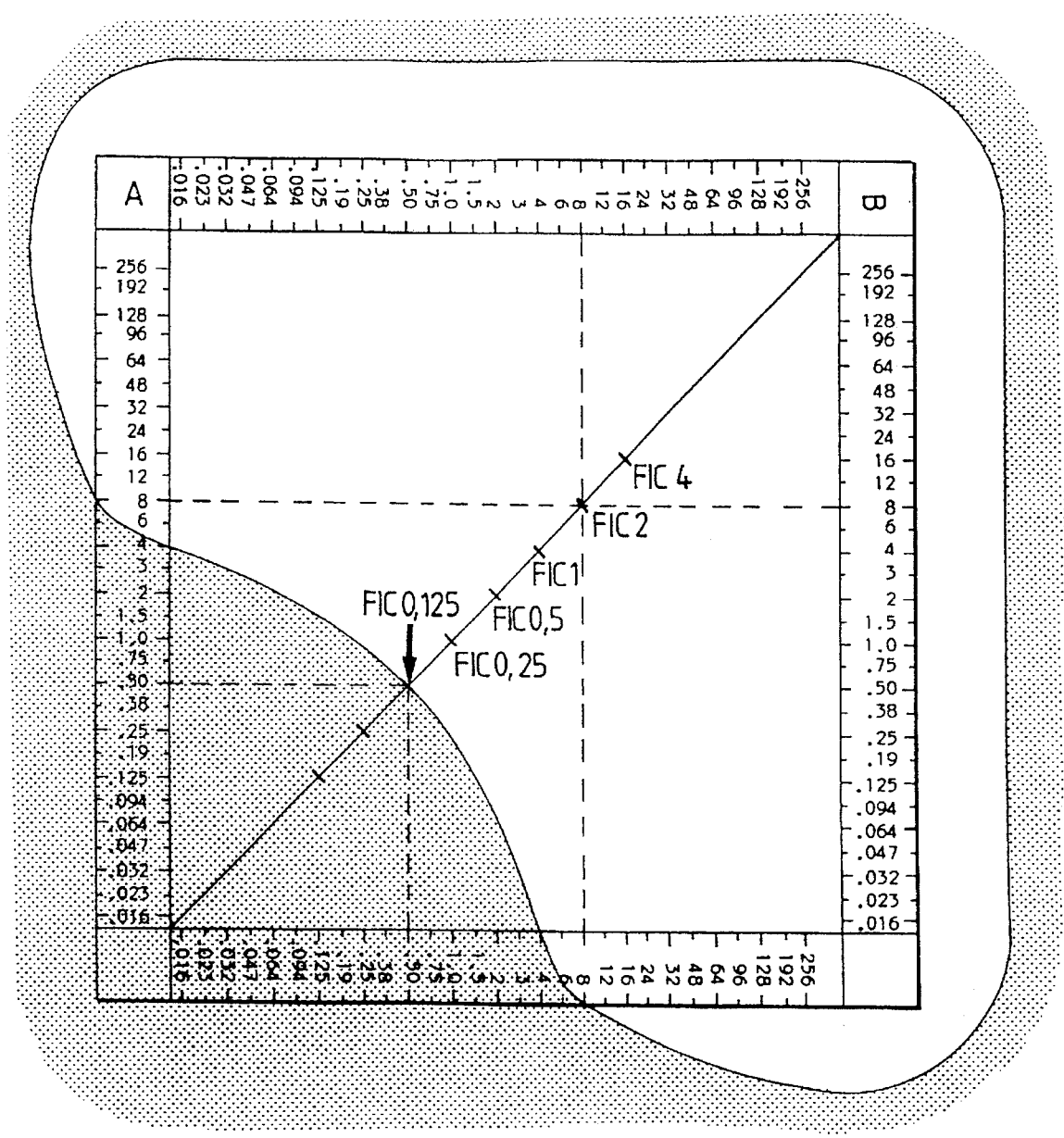
FIG. 7 shows the quantification of interactions between substances and FIG. 8 the interaction between growth promoters.

FIGS. 5 A, B, C and D show schematically the interpretation of the interactions of for example two antibiotics (A and B). Growth of a microorganism is indicated with dots, whereas the inhibition zone, i.e. where no growth occurs, is blank. The broken lines in these figures, as well as in FIGS. 6 and 7, are merely shown for illustrative purpose, to facilitate the reading of the results. The broken lines represent the MIC (minimum inhibition concentration) or MBC (minimum bactericidal concentration) values of the individual substances. From these figures it is evident that the deepest point of the indentation (shown with an arrow) in the inhibition zone indicates the point of maximum interaction between the substances tested. FIG. 5A shows an indifferent effect and 5B an additive effect of the substances tested. FIG. 5 C shows an antagonistic effect and FIG. 5 D a synergistic effect of the substances tested. FIG. 5 E shows effect of a third substance C on the same two substances A and B of FIG. 5 D. Substance C has been applied in an even concentration within the quadrate test area of the agar plate. Thereafter substances A and B have been applied as in FIG. 5 D. Substance C antagonized the activity of substance A and is indifferent to the activity of B. Overall substance C counteracts the synergistic interaction of A and B, as is evident from FIG. 5 E.

FIGS. 6 A and B show how bactericidal interactions can be studied. This can be done either by replicating the inhibitory growth pattern (FIG. 6 A) using a velvet pad or comparable device onto a drug free plate or inactivating the antibiotic present in the agar using specific antibiotic inactivating chemicals such as sodium polyanethol sulphate to inactivate aminoglycosides or enzymes e.g. β-lactamase to inactivate β-lactam antibiotics, and then to further reincubate the test plate. In the absence of antibiotic, bacterial cells which were inhibited but were fully viable will now grow within the inhibition zone giving a new growth pattern reflecting the bactericidal or killing effects of the antibiotic combination (FIG. 6 B). FIG. 6 A thus illustrates the inhibitory growth pattern whereas FIG. 6 B illustrates the killing pattern. In the example shown the inhibitory growth pattern shows an indifferent interaction between the substances tested whereas the killing pattern shows that the bactericidal interaction of the two substances results in synergism.

FIG. 7 shows how results are to be interprated and quantified. The interaction between the compounds (e.g. two antibiotics) are quantified and the different values read with the aid of the reading scales. When quantifying and interpreting antibiotic interactions, the MIC or MBC values of the individual antibiotics when used singly are compared to the concentration of the agents when used as a combination. These values are then used to calculate the fractional inhibitory concentration (FIC) or fractional bactericidal concentration (FBC) index using the following equations:

$$FIC = FIC_A + FIC_B = \frac{C_{A/B}}{MIC_A} + \frac{C_{B/A}}{MIC_B}$$

in which A and B are two substances, $C_{A/B}$ is the concentration of A in the presence of B and $C_{B/A}$ is the concentration of B in the presence of A at the point of maximum interaction. $MIC_A$ is the minimum inhibitory concentration of A and $MIC_B$ is that of B.

$$FBC = FBC_A + FBC_B = \frac{C_{A/B}}{MBC_A} + \frac{C_{B/A}}{MBC_B}$$

wherein A, B, $C_{A/B}$ and $C_{B/A}$ are as defined above, whereas $MBC_A$ is the minimum bactericidal concentration of A and $MBC_B$ is that of B. These definitions are illustrated by Krogstad et al in Antibiotics in Laboratory Medicine, Lorian 1986, page 545.

A gradient of FIC indices can be determined along the diagonal of the reading scale (see FIG. 7) or along a line parallel to the diagonal. According to accepted definitions, an FIC index of $\leq 0.5$ indicate synergy, $-1$ indifference or additivity and $\leq 2.0$ antagonism. The combined effects of A and B can thus be directly interpreted and quantified in terms of an FIC index by reading the point of intersection between the zone edge inside the checkerboard and the diagonal of the FIC index gradient. In the example shown the MIC values of the individual antibiotics A and B can be read from the intersections of the zone edges with the vertical and horizontal scales respectively. The point of optimal interaction in FIG. 7, i.e. the maximum indentation of the inhibition pattern as indicated with an arrow, gives a $C_{A/B}$ of 0.5 µg/ml and $C_{B/A}$ of 0.5 µg/ml. Further in the example shown in FIG. 7 $MIC_A$ is 8 µg/ml and $MIC_B$ 8 µg/ml. According to the equation above this gives:

$$FIC = \frac{0.5}{8} + \frac{0.5}{8} = 0.125$$

In this example an FIC index of 0.125 is directly obtained by simply reading the intersection of the zone edge with the FIC index gradient, giving an immediate quantitative answer about the synergistic interaction of the substances A and B.

When performing "checkerboard" determinations according to the present invention the FIC values can be directly read at the maximum indentation of the inhibition pattern against a FIC scale that can be preprinted on the test carrier or present as a separate reading scale.

Figure 8:
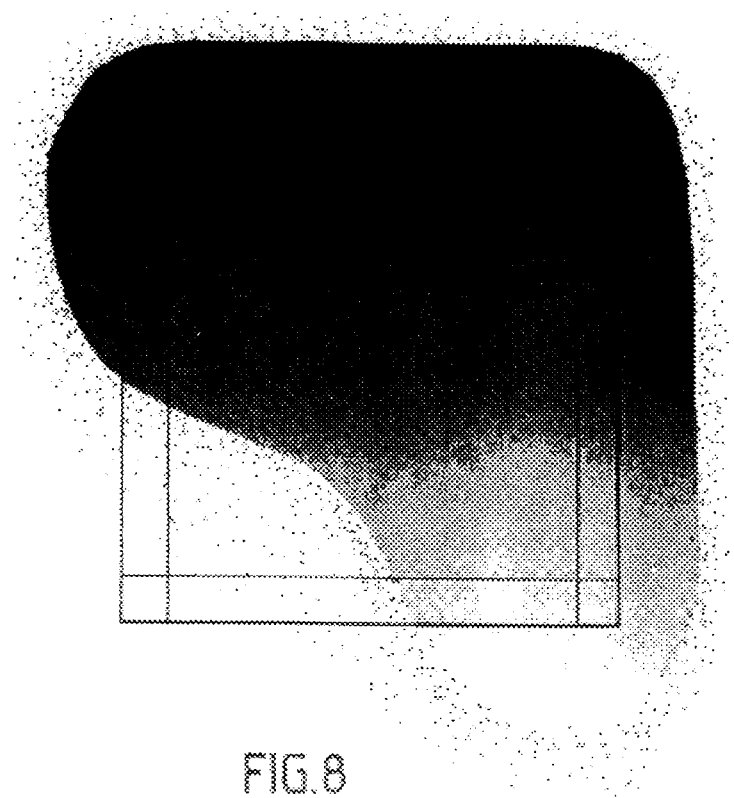

When studying interactions between growth promoters and other nutrients, similar models as described for antibiotic combinations can be used. FIG. 8 illustrates a growth pattern where enhanced growth density indicate the concentrations necessary to support growth as well as the concentrations and ratios of the two substances where their interactive effects are optional.

The term "microorganism" refers to bacteria, such as enterobacteriaceae, staphylococci, streptococci, hemofilus, neisseriaceae, bacteroides and clostridia, mycobacteria, actinomyces, mycoplasma, nocardia, virus, and fungi such as moulds, yeast and candida.

The term "biological cells" comprises cancer cells, normal human cells, animals cells and plant cells, of the type "stem cells".

The term "substance" as used here refers to both growth promoters and growth inhibitors, as well as substances that per se do not have an inherent activity but a potentiating (synergistic) or antagonistic effect on the activity of another substance. Examples of growth inhibitors are antimicrobial substances such as antibiotics, for example aminoglycosides, β-lactam antibiotics, macrolide antibiotics, polymyxins, polypeptides and other chemotherapeutical agents such as sulfonamides, antimycotics, for example 5-fluorocytosine, amphotericin, antiviral agents such as adenine arabinoside (Ara-A), trifluorothymidine; anti-tuberculous drugs, such as isoniazide and cycloserine; anti-cancer agents, such as cyclophosphamide, methotrexate, 5-fluorouracil and mitomycin, disinfectants, antiseptics and preservatives such as chloro hexidine, ethanol and benzalkonium chloride. Substances such as β-lactamase enzyme inhibitors, e.g. clavulanic acid and pH-regulating compounds, e.g. buffers, may enhance or reduce the effects of other substances despite an inherent lack of activity.

Growth promoters are substances such as vitamins, hormones, amino acids and trace elements while nutrients include carbohydrates, peptones, nitrogen compounds and fatty acids. Drugs which may have carcinogenic, mutagenic and teratogenic effects include cyclophosphamide, hydroxylamine and methotrexate.

What is claimed is:

1. A device for quantitative determination of the interacting effects of two or more substances having growth inhibiting or growth promoting effects on microorganisms or biological cells grown on a solid medium, said device comprising an inert, non-porous carrier on which at least two substances are applied within a quadrate test area on all or part of a surface of the carrier to be contacted with said medium, and wherein two or more substances are present on the quadrate test area in such a manner that the first substance exhibits a concentration gradient from one edge to the opposite edge of the quadrate test area with a concentration minimum along one edge and a concentration maximum along the opposite, second edge of the quadrate test area, while the second substance exhibits a concentration gradient extending in a direction perpendicular to that of the first substance, having a concentration minimum along a third edge and a concentration maximum along the opposite, fourth edge of the quadrate test area, so that when the carrier is applied to the surface of the medium, the concentration gradients are transferred to the surface of the medium promoting pattern thereon, so that a quantitative determination of the growth inhibiting or growth promoting effects of the substances can be made from the pattern formed by the substances.

2. The device of claim 1 further comprising a reading scale integrated onto the non-substance side of the carrier.

3. The device of claim 2, further comprising a scale for reading the concentration of each substance and a scale for reading fractional inhibitory concentration index and/or fractional bactericidal concentration index.

4. A device for quantitative determination of the interacting effects of three or more substances having growth inhibiting or growth promoting effects on microorganisms or biological cells grown on a solid medium, said device comprising: an inert, non-porous carrier on which at least three substances are applied within a quadrate test area on all or part of a surface of the carrier to be contacted with said medium, wherein three or more substances are present on the quadrate test area in such a manner that the first substance exhibits a concentration gradient from one edge to the opposite end of the quadrate test area, with a concentration minimum along one edge and a concentration maximum along the opposite, second edge of the quadrate test area, while the second substance exhibits a concentration gradient extending in a direction perpendicular to that of the first substance, having a concentration minimum along a third edge and a concentration maximum along the opposite, fourth edge of the quadrate test area, and superimposed directly on top of the first and second substances is at least a third substance which exhibits a concentration gradient having a concentration minimum and maximum opposing edges of the quadrate test area, so that when the carrier is applied to the surface of the medium, the concentration gradients are transferred to the surface of the medium forming an inhibition or promoting pattern thereon, so that a quantitative determination of the growth inhibiting or growth promoting effects of the substances can be made from the pattern formed by the substances.

5. A device for quantitative determination of the interacting effects of two or more substances having growth inhibiting or growth promoting effects on microorganisms or biological cells grown on a solid medium, comprising an inert, non-porous carrier on which at least two substances are applied on a quadrate test area on all or part of a surface of the carrier, wherein the first substance is applied in a uniform concentration over the entire quadrate test area, and wherein a second substance exhibits a concentration gradient having a concentration minimum along one edge and a concentration maximum along the opposite edge of the quadrate test area so that when the carrier is applied to the surface of the medium, the concentration gradients are transferred to the surface of the medium forming an inhibition or promoting pattern thereon, so that a quantitative determination of the growth inhibiting or growth promoting effects of the substances can be made from the pattern formed by the substances.

6. The device of claim 5, further comprising a reading scale integrated onto the non-substance side of the carrier.

7. The device of claim 6, further comprising a scale for reading the concentration of each substance and a scale for reading fractional inhibitory concentration index and/or fractional bactericidal concentration index.

8. A device for quantitative determination of the interacting effects of three or more substances having growth inhibiting or growth promoting effects on microorganisms or biological cells grown on a solid medium, comprising an inert, non-porous carrier on which at least three substances are applied on a quadrate test area on all or part of a surface of the carrier, wherein the first substance is applied in a uniform concentration over the entire quadrate test area and a second substance exhibits a concentration gradient having a concentration minimum along one edge and a concentration maximum along the opposite edge of the quadrate test area, and wherein superimposed directly on top of the first and second substances is at least a third substance which exhibits a concentration gradient having a concentration minimum and maximum along opposing edges of the quadrate test area so that when the carrier is applied to the surface of the medium, the concentration gradients are transferred to the surface of the medium forming an inhibition or promoting pattern thereon, so that a quantitative determination of the growth inhibiting or growth promoting effects of the substances can be made from the pattern formed by the substances.

9. A method for quantitative determination of the interacting effects of two or more substances on the promotion or inhibition of growth of microorganisms or biological cells grown on a solid medium, said method comprising the steps of:

contacting the surface of a solid medium in which microorganisms or biological cells are grown with a device such that a predefined concentration gradient is transferred to said contacted solid medium, said device comprising an inert, non-porous carrier having at least two substances within a quadrate test area on all or part of a surface of the carrier, wherein a first substance exhibits a concentration gradient from one edge to the opposite edge of said quadrate area, with a concentration minimum along a first edge and a concentration maximum along a second opposite edge of said quadrate test area, and wherein a second substance exhibits a concentration gradient extending in a direction perpendicular to the concentration gradient of the first substance, with a concentration minimum along a third edge and a concentration maximum along the opposite fourth edge of said quadrate test area;

incubating the contacted solid medium; and quantitatively determining the concentration of each substance at relevant end points from an inhibition or promotion pattern formed by the substances showing the effect of cellular inhibition, cell killing or cellular growth by reading scales that are adapted to the predefined concentration gradient of each substance.

10. The method of claim 9, further comprising applying a third substance within the same quadrate test area on the surface of the solid medium as the first and second substances, wherein the applied substance exhibits a concentration gradient having a concentration minimum and maximum along opposite edges of the quadrate test area.

11. The method of claim 10, wherein the pattern of the concentration gradient of each substance is applied simultaneously on the surface of the solid medium.

12. The method of claim 9, wherein the pattern of the concentration gradient of each substance is applied simultaneously on the surface of the solid medium.

* * * * *